United States Patent [19]

Caputo et al.

[11] Patent Number: 5,288,460

[45] Date of Patent: * Feb. 22, 1994

[54] PLASMA CYCLING STERILIZING PROCESS

[75] Inventors: Ross A. Caputo, Long Grove; Jeffrey Jones, Antioch, both of Ill.; Kern A. Moulton, Livermore, Calif.; Bryant A. Campbell, deceased, late of Los Gatos, Calif., Louise A. Campbell, legal representative

[73] Assignee: Abtox, Inc., Mundelein, Ill.

[*] Notice: The portion of the term of this patent subsequent to Feb. 16, 2010 has been disclaimed.

[21] Appl. No.: 962,895

[22] Filed: Oct. 19, 1992

Related U.S. Application Data

[63] Continuation-in-part of Ser. No. 576,294, Aug. 31, 1990, Pat. No. 5,186,893, which is a continuation-in-part of Ser. No. 475,602, Feb. 6, 1990, abandoned, which is a continuation-in-part of Ser. No. 321,483, Mar. 8, 1989, abandoned.

[51] Int. Cl.$^5$ ............................................... A61L 2/00
[52] U.S. Cl. ........................................ 422/23; 422/22; 422/28; 422/32; 422/33
[58] Field of Search .................. 422/22, 23, 28, 32-33, 422/90, 29, 186.04-186.06

[56] References Cited

U.S. PATENT DOCUMENTS

| | | |
|---|---|---|
| 3,383,163 | 5/1968 | Menashi . |
| 3,410,776 | 11/1968 | Bersin . |
| 3,428,548 | 2/1969 | Hollahan . |
| 3,704,096 | 11/1972 | Verses et al. ........................ 422/22 |
| 3,737,608 | 6/1973 | Nagao et al. ..................... 219/10.55 |
| 3,851,436 | 12/1974 | Fraser et al. ........................ 422/22 |
| 3,948,601 | 4/1976 | Fraser et al. ........................ 422/22 |
| 4,065,369 | 12/1977 | Ogawa et al. ...................... 204/164 |
| 4,123,663 | 10/1978 | Horiike .............................. 250/531 |
| 4,138,306 | 2/1979 | Niwa .................................. 156/345 |
| 4,151,034 | 4/1979 | Yamamoto et al. ............... 156/345 |
| 4,160,690 | 7/1979 | Shibagaki et al. ................. 156/643 |
| 4,169,123 | 9/1979 | Moore et al. ...................... 422/29 |
| 4,169,124 | 9/1979 | Forstrom et al. .................. 422/33 |
| 4,203,943 | 5/1980 | Gillis et al. ........................ 422/27 |
| 4,207,286 | 9/1980 | Boucher ............................. 422/21 |
| 4,230,663 | 10/1980 | Forstrom et al. .................. 422/33 |
| 4,241,010 | 12/1980 | Baran .................................. 422/2 |
| 4,289,728 | 9/1981 | Peel et al. .......................... 422/24 |
| 4,321,232 | 3/1982 | Bithell ................................ 422/23 |
| 4,348,357 | 9/1982 | Bithell ................................ 422/22 |
| 4,366,125 | 12/1982 | Kodera et al. .................... 422/295 |
| 4,437,567 | 3/1984 | Jeng et al. ......................... 206/210 |
| 4,643,876 | 2/1987 | Jacobs et al. ....................... 422/22 |
| 4,801,427 | 1/1989 | Jacob .................................. 422/23 |
| 4,818,488 | 4/1989 | Jacob .................................. 422/23 |
| 4,881,326 | 11/1989 | May ..................................... 34/92 |
| 4,898,715 | 2/1990 | Jacob .................................. 422/23 |
| 4,917,586 | 4/1990 | Jacob .................................. 422/23 |
| 4,931,261 | 6/1990 | Jacob .................................. 422/23 |
| 4,943,417 | 7/1990 | Jacob .................................. 422/23 |
| 4,976,920 | 11/1990 | Jacob .................................. 422/23 |
| 5,068,087 | 11/1991 | Childers ............................. 422/26 |
| 5,178,829 | 1/1993 | Moulton et al. ................... 422/23 |
| 5,186,893 | 2/1993 | Moulton et al. ................... 422/23 |

FOREIGN PATENT DOCUMENTS 58-103460 6/1983 Japan .
58-162276 9/1983 Japan .

Primary Examiner—Robert J. Warden
Assistant Examiner—Krisanne M. Thornton
Attorney, Agent, or Firm—Majestic, Parsons, Siebert & Hsue

[57] ABSTRACT

A method for plasma sterilization within a controlled temperature range includes exposing the interior of a chamber and any articles therein to a gas plasma flowing from a plasma generating chamber until the temperature in the chamber rises to a preselected maximum temperature. The flow of the plasma gas to the chamber is terminated when the temperature in the chamber falls to a temperature below the preselected maximum temperature. These steps are repeated until sterilization of the interior of the chamber or any articles therein is effected. The temperature below the preselected maximum temperature when gas plasma flow is again initiated is preferably not more than 3° C. below the preselected maximum temperature. The gas plasma can be generated from a gas mixture that includes oxidizing and/or reducing agents. Preferably the pressure in the sterilizing chamber rises to from 0.1 to 10 torr when the gas plasma is flowing into the chamber, and the pressure in the sterilizing chamber falls to a lower pressure when the gas plasma flow into the sterilizing chamber is terminated. The articles to be sterilized include the interior of a vessel or chamber. The vessel or chamber itself serves as a sterilizing chamber and connects to the plasma generating chamber.

24 Claims, 10 Drawing Sheets

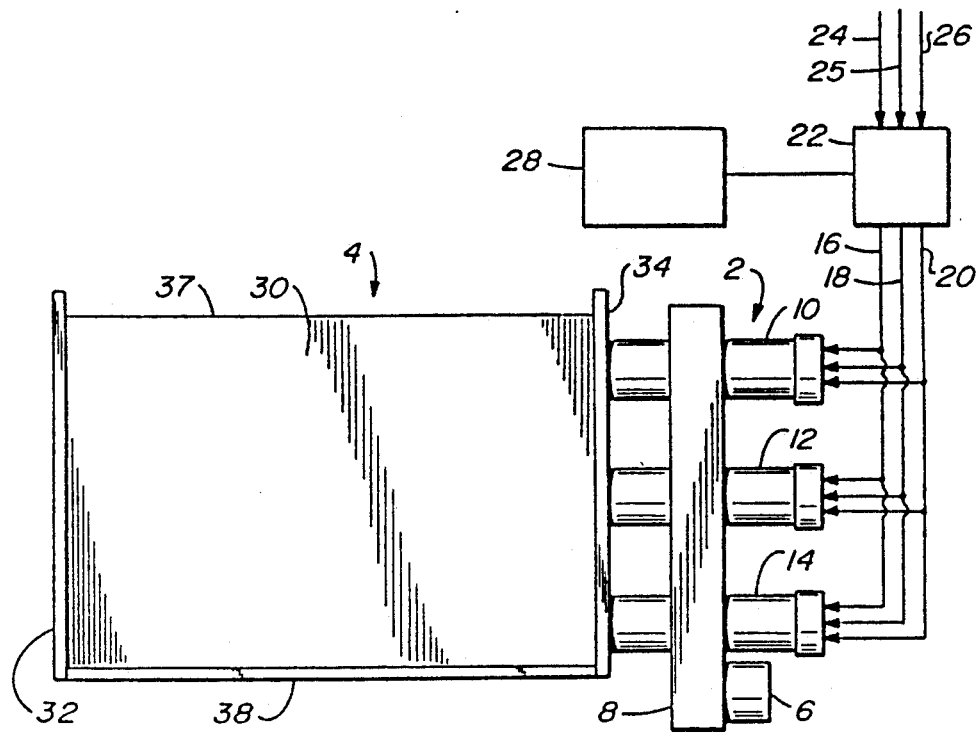
FIG._1
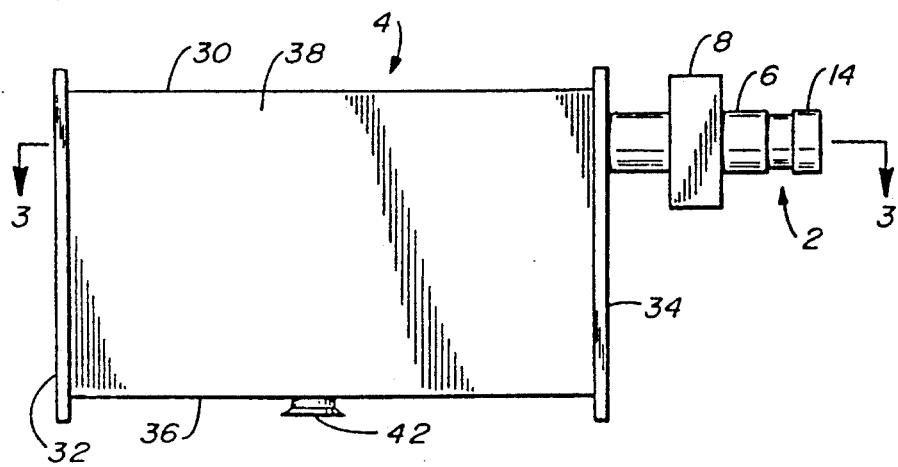
FIG._2

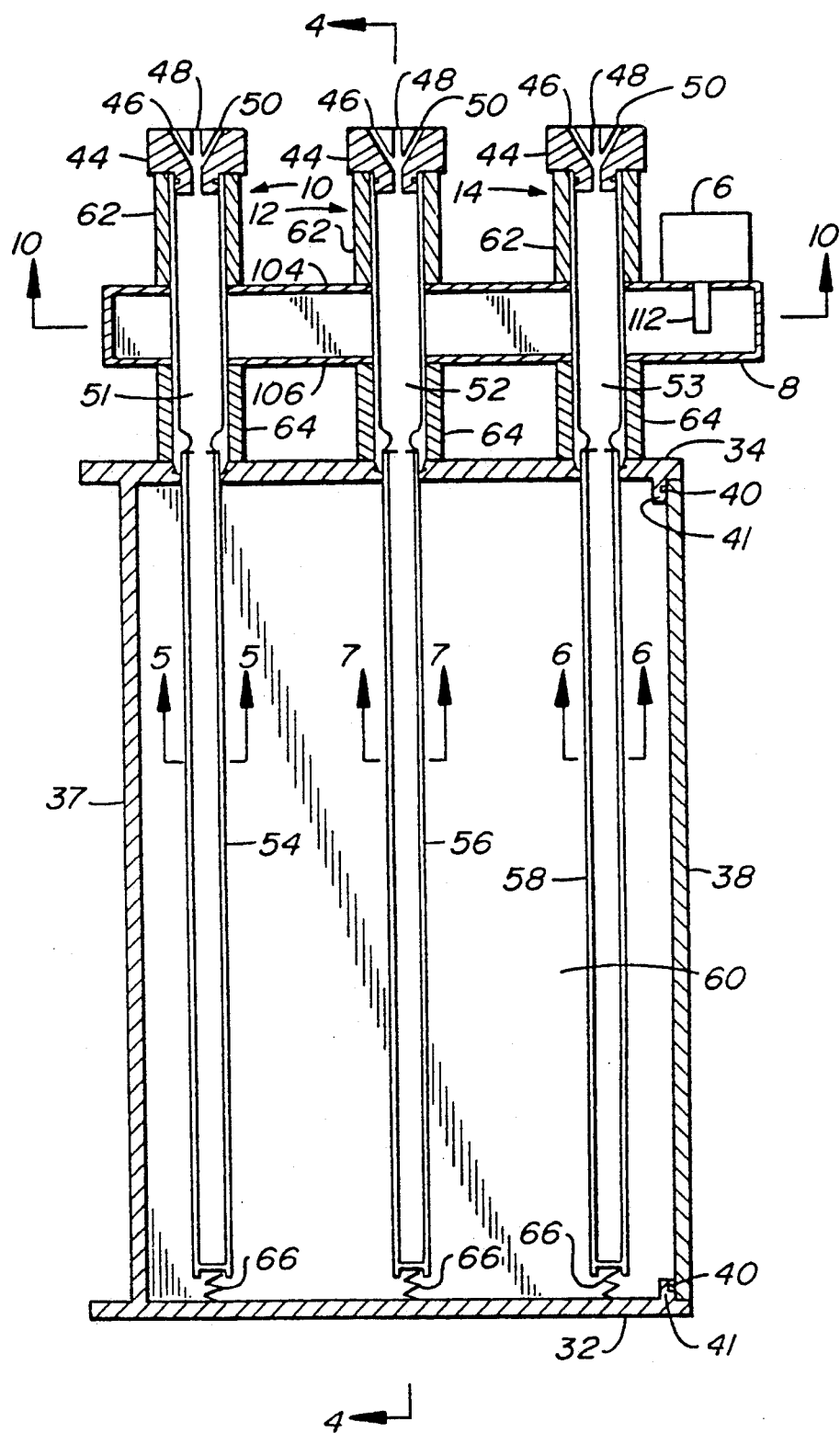
FIG._3

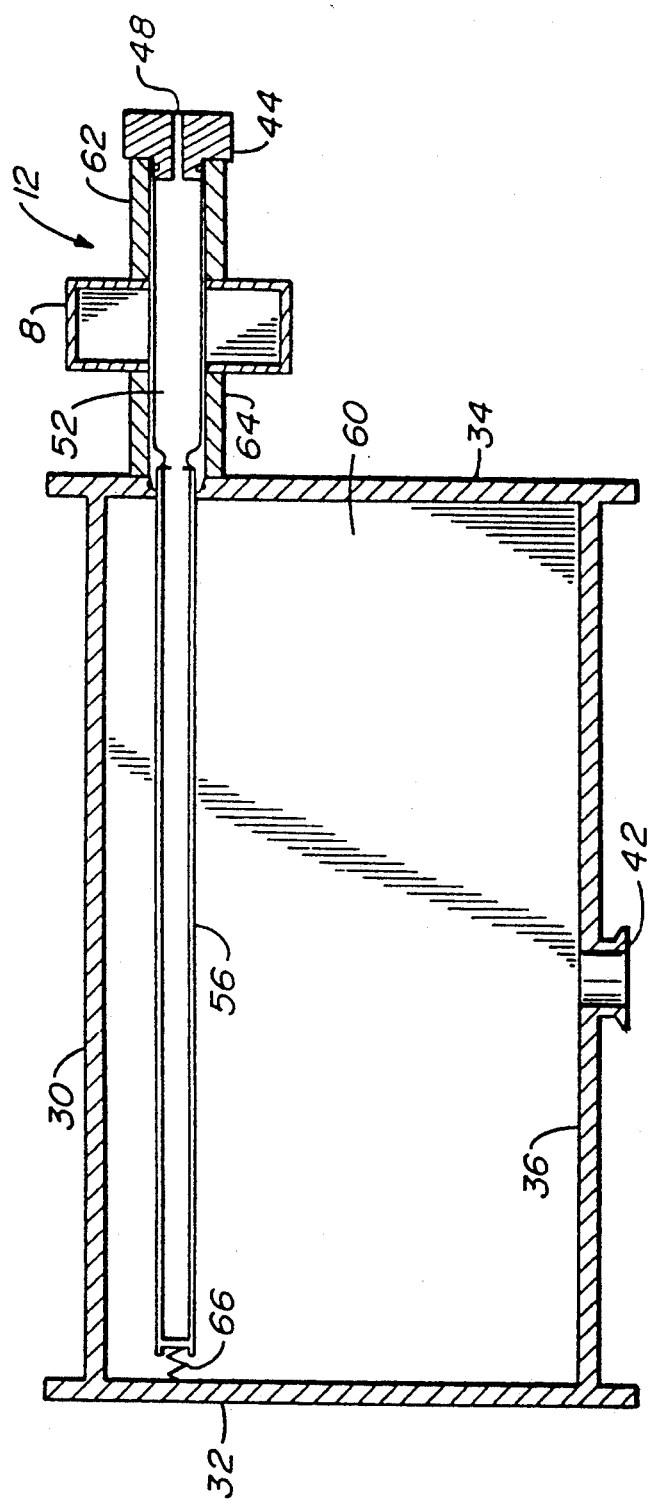
FIG._4
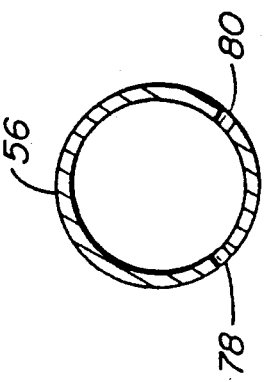
FIG._7
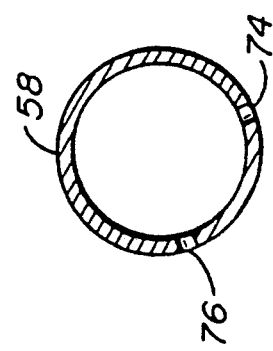
FIG._6
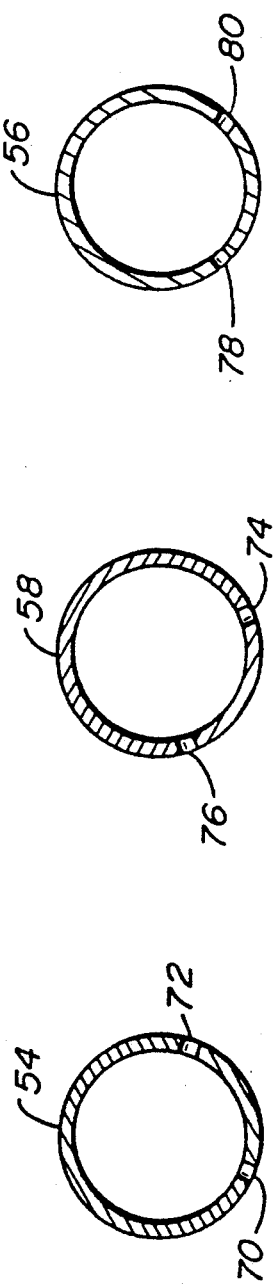
FIG._5

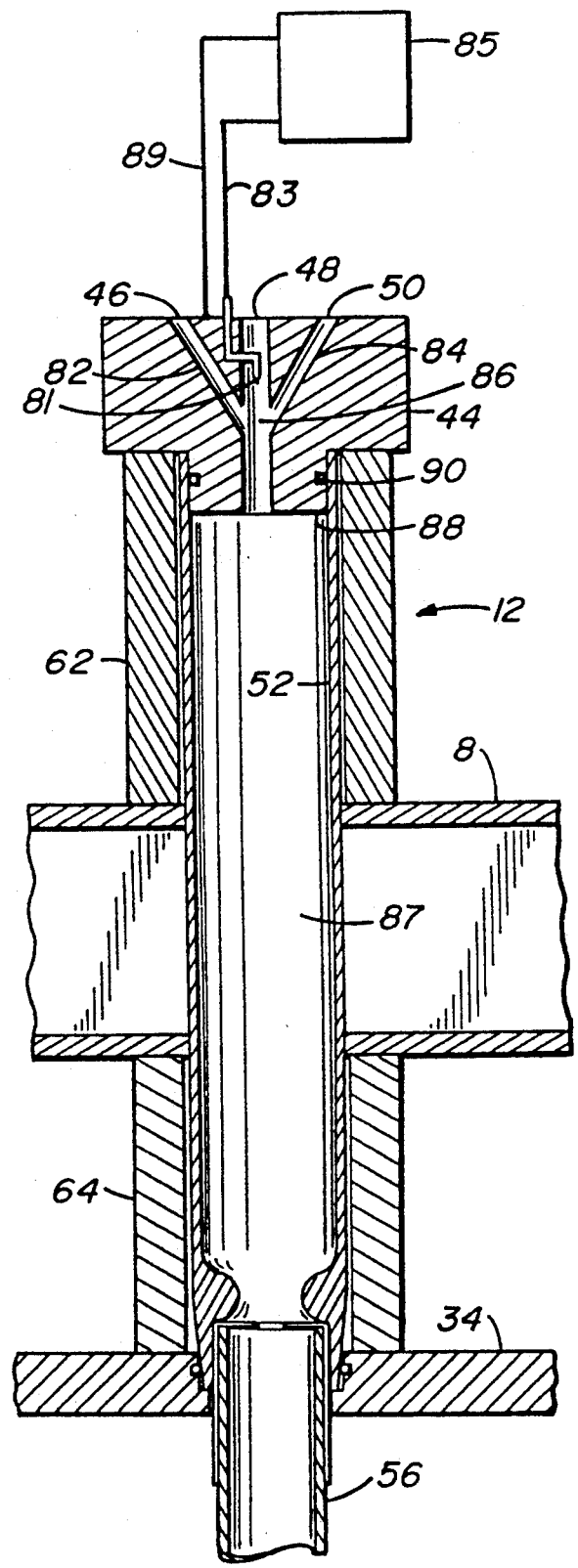
FIG._8

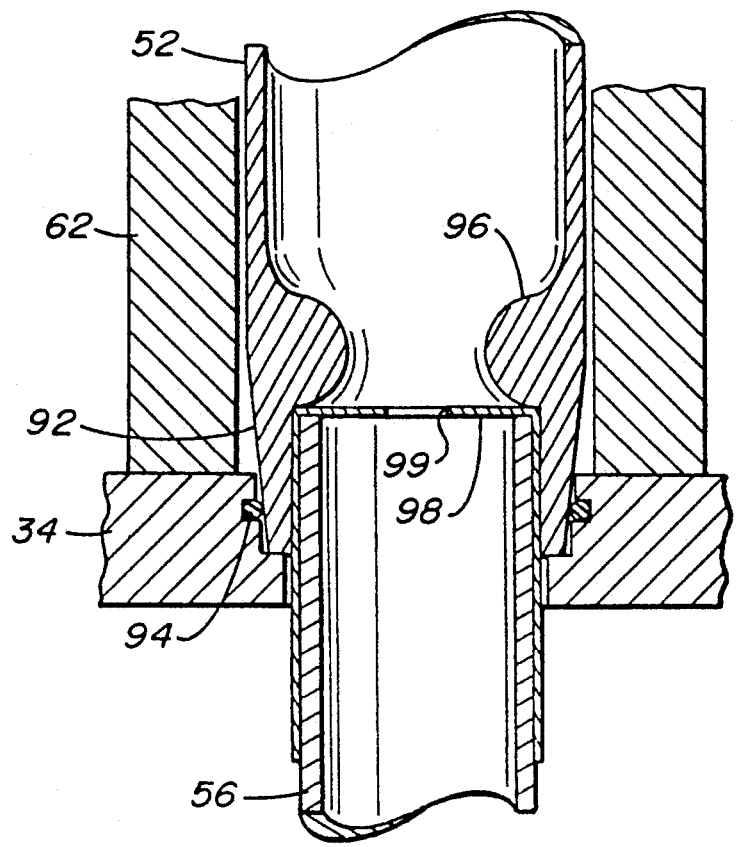
FIG._9
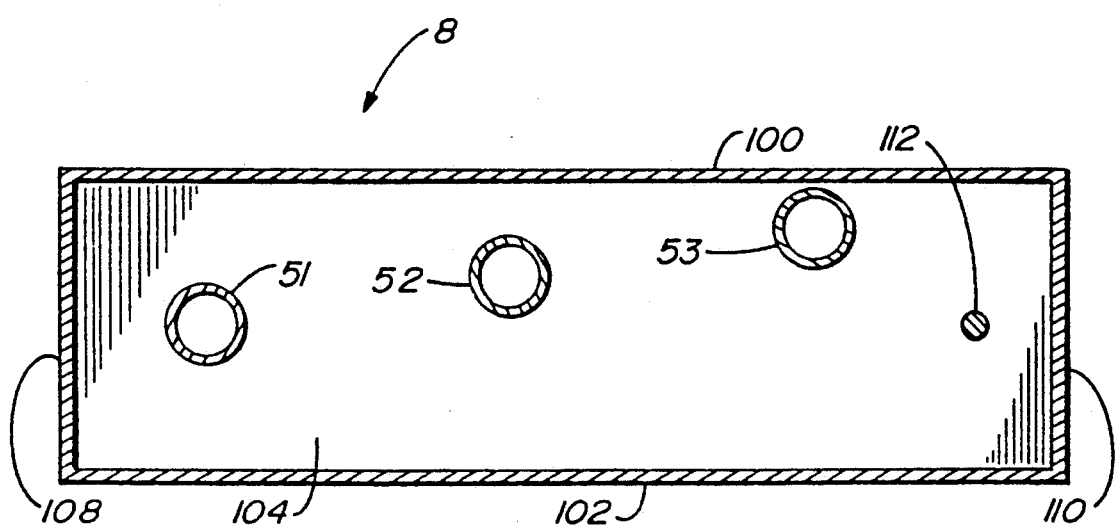
FIG._10

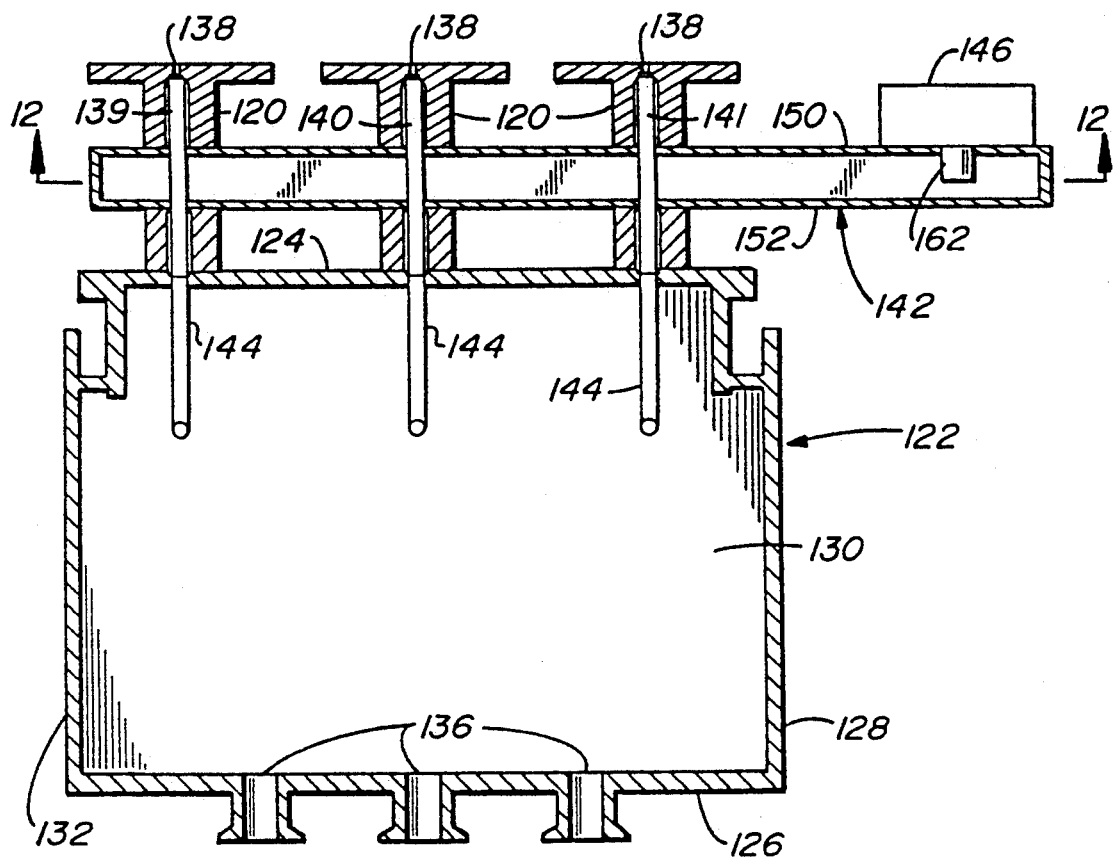
FIG._11
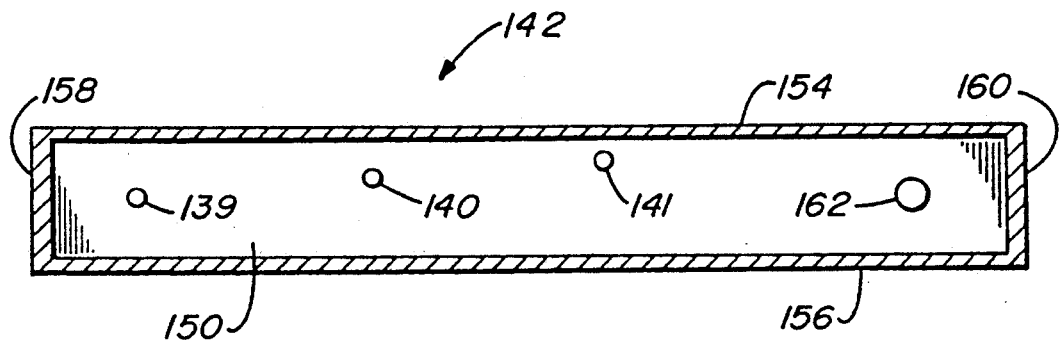
FIG._12

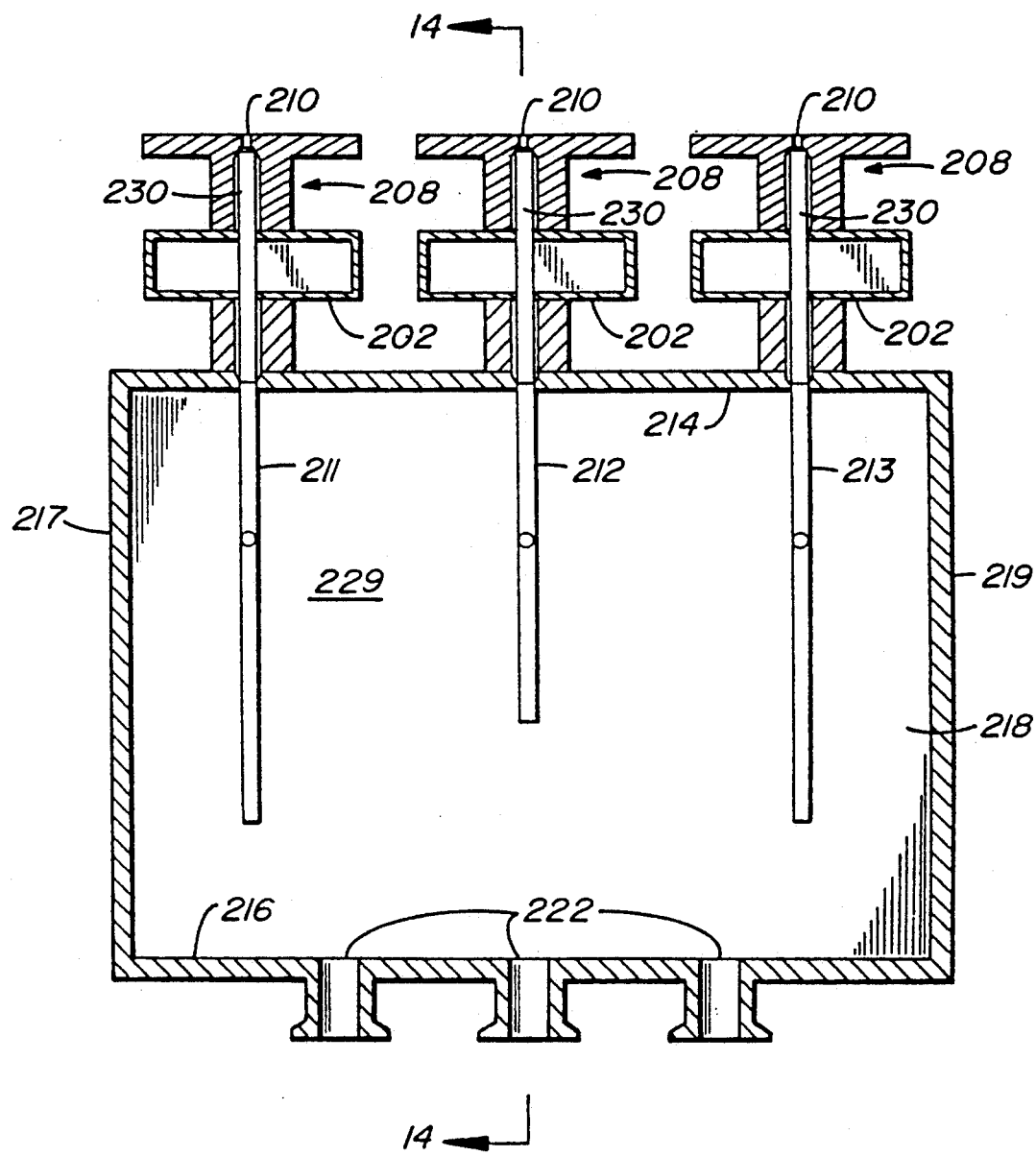
FIG._13

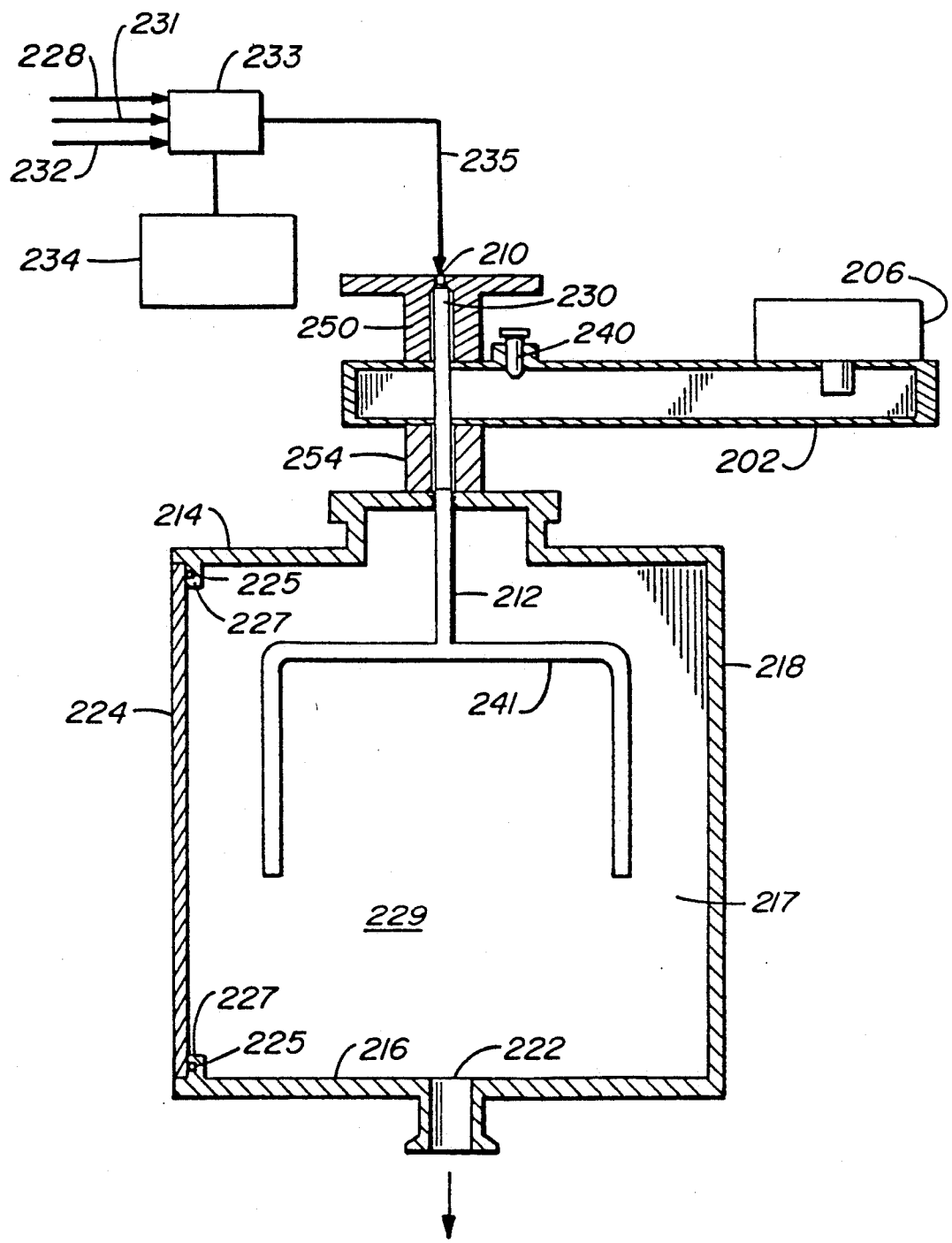
FIG._14

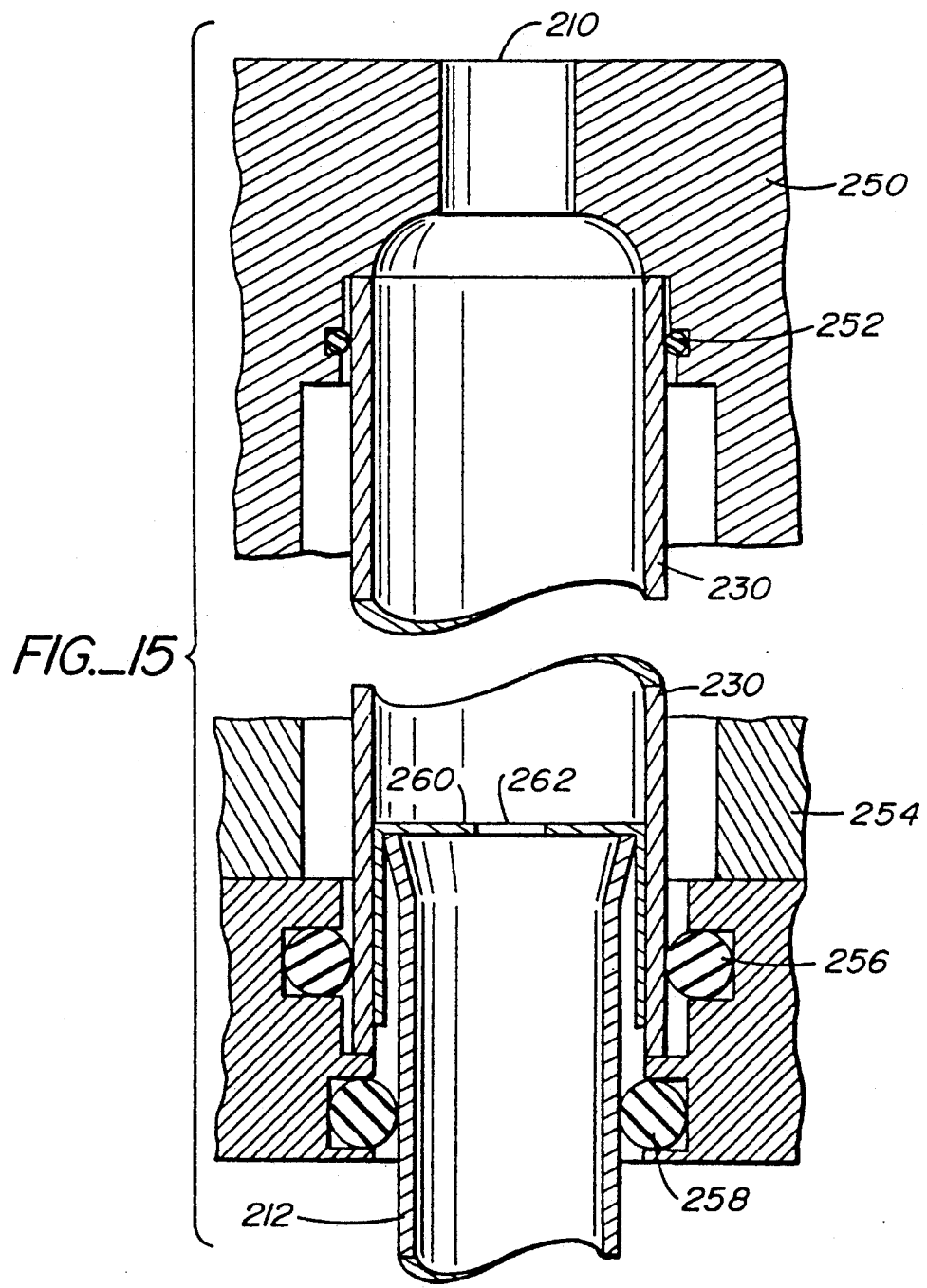
FIG._15

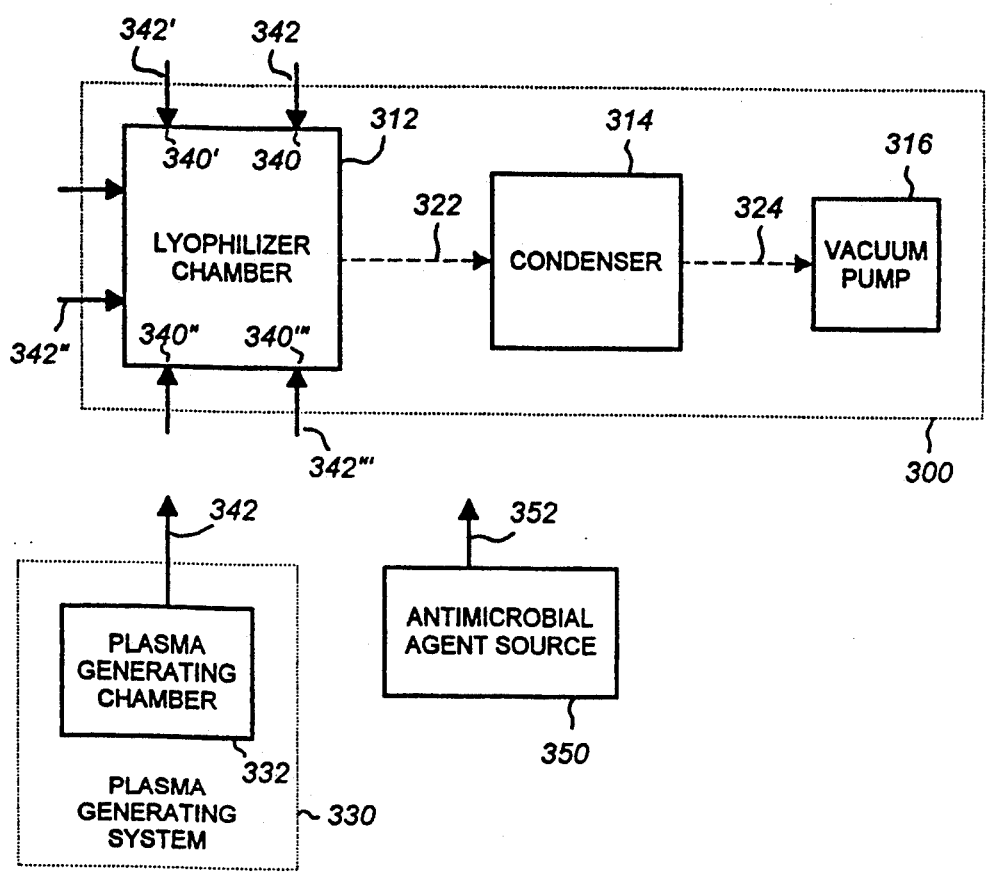
FIG._16

PLASMA CYCLING STERILIZING PROCESS

RELATIONSHIP TO COPENDING APPLICATIONS

This application is a continuation-in-part of copending application Ser. No. 07/576,294, now U.S. Pat. No. 5,186,893 filed Aug. 31, 1990, which is a continuation-in-part of application Ser. No. 07/475,602 filed Feb. 6, 1990 now abandoned, which is a continuation-in-part of application Ser. No. 07/321,483 filed Mar. 8, 1989 now abandoned.

The entire contents of the following commonly assigned, copending applications and issued patents relating to the subject matter of this invention are hereby incorporated by reference: application Ser. No. 07/576,325, now U.S. Pat. 5,178,829 filed Aug. 31, 1990 by K. A. Moulton, R.A. Caputo and B.A. Campbell entitled FLASH STERILIZATION WITH PLASMA. U.S. Pat. No. 5,084,239 by K.A. Moulton, R.A. Caputo and B.A. Campbell entitled PLASMA STERILIZING PROCESS WITH PULSED ANTIMICROBIAL AGENT TREATMENT. Application Ser. No. 07/589,511 now U.S. Pat. No. 5,184,046 filed Sep. 28, 1990 by Bryant A. Campbell entitled CIRCULAR WAVEGUIDE PLASMA MICROWAVE STERILIZER APPARATUS. U.S. Pat. No. 5,115,166 by K.A. Moulton and B.A. Campbell entitled PLASMA STERILIZER AND METHOD.

This invention relates to sterilization of articles with gaseous plasmas. In particular this invention relates to a method for controlling the temperature during sterilizing of the interior of chambers and/or articles in the chambers with a cycled gas plasma.

BACKGROUND OF THE INVENTION

A variety of gas sterilization methods has been investigated in the past. Methods using ethylene oxide and other disinfecting gases are widely used for sterilizing a wide range of medical products from pharmaceutical preparations to surgical instruments. Irradiation alone or together with disinfecting gases has also been investigated, as summarized by Russell, A. THE DESTRUCTION OF BACTERIAL SPORES. New York: Academic Press (1982).

A sterilizing method must effectively kill all organisms, including spores, without damage to the article or goods being sterilized. However, many disinfecting gases which meet this criterion, such as ethylene oxide and irradiation methods have been recognized to expose workers and the environment to safety hazards. States and Federal legislation are severely restricting the amount of hazardous gases such as ethylene oxide (a carcinogen) in the working environment, or the use of any system or method which produces toxic residues or exhaust products. This is presenting a major crisis in hospitals and other areas of the health industry.

DESCRIPTION OF THE PRIOR ART

The use of plasma to sterilize containers was suggested in U.S. Pat. No. 3,383,163. Plasma is an ionized body of gas which may be generated by the application of power from different sources. The ionized gas will contact microorganisms on the surfaces of the items to be sterilized and effectively destroy the microorganisms.

Sterilizing plasmas have been generated with a wide variety of gases: argon, helium or xenon (U.S. Pat. No. 3,851,436); argon, nitrogen, oxygen, helium or xenon (U.S. Pat. No. 3,948,601); glutaraldehyde (U.S. Pat. No. 4,207,286); oxygen (U.S. Pat. No. 4,321,232); oxygen, nitrogen, helium, argon or Freon with pulsed pressure (U.S. Pat. No. 4,348,357); hydrogen peroxide (U.S. Pat. No. 4,643,876); nitrous oxide, alone or mixed with oxygen, helium or argon (Japanese Application Disclosure No. 103460-1983); and nitrous oxide, alone or mixed with ozone (Japanese Application No. 162276-1983). Unfortunately, these plasmas have proven to be too corrosive to articles being sterilized, and particular packaging materials; have left toxic residues on the sterilized articles; or have presented safety or environmental hazards.

Non-plasma gas sterilization procedures have been described using ozone (U.S. Pat. No. 3,704,096) and hydrogen peroxide (U.S. Pat. Nos. 4,169,123, 4,169,124, 4,230,663, 4,366,125, 4,289,728, 4,437,567 and 4,643,876). These materials are toxic and leave undesirable residues.

Plasma gas sterilizer systems described in U.S. Pat. Nos. 3,851,436 and 3,948,601 comprise separate plasma RF generation chamber and sterilizing chamber. A gas plasma produced in the plasma generating chamber with argon, helium, nitrogen, oxygen or xenon is passed into a separate sterilization vacuum chamber. U.S. Pat. No. 4,643,876 describes a hydrogen peroxide plasma RF generation chamber which also functions as the sterilizing chamber. Matching networks are required with the RF systems to adjust to the conductivity variations in the plasma generating zone.

OBJECTS AND SUMMARY OF THE INVENTION

It is an object of this invention to provide an improved plasma sterilizing process which carries out effective sterilization quickly, with no toxic residues and with emissions which present no environmental safety hazard and without damage to non-metallic articles and packaging materials.

It is another object of this invention to provide an economical sterilizing process which is safe and effective for use in a hospital environment.

It is another object of the present invention to provide an efficient process which achieves sterilization with all types of articles used in the health care environment, including metallic articles and articles contained in porous sterilization packaging including cellulosic materials.

It is also another object of the present invention to provide an efficient and cost-effective process for sterilization of vessels or chambers such as lyophilizers.

It is a still further object of this invention to provide effective sterilization at a selected maximum temperature, with an effective kill rate, and with non-explosive gas mixtures containing hydrogen and/or oxygen.

These and additional objects are accomplished by the method of this invention for plasma sterilization within a controlled temperature range. The method comprises exposing an article in a sterilizing chamber to a gas plasma flowing from a plasma generating chamber until the temperature in the sterilizing chamber rises to a preselected maximum temperature; terminating flow of the gas plasma to the sterilizing chamber until the temperature in the sterilizing chamber falls to a temperature below the preselected maximum temperature; and repeating these steps until sterilization of the article is effected.

Preferably, the pressure in the sterilizing chamber rises to from 0.1 to 10 torr when the gas plasma is flowing into the chamber and falls to a lower pressure when the gas plasma flow into the sterilizing chamber is terminated. Optimally, the pressure in the sterilizing chamber rises to above 1 torr when the gas plasma is flowing into the chamber and falls to a pressure of less than 1 torr when the gas flow into the chamber is terminated.

The gas plasma is preferably generated from a gas mixture that includes oxidizing and/or reducing agents. The mixture of gases preferably consists essentially of argon, helium, nitrogen or mixtures thereof; from 1 to 21 (v/v) % oxygen; and from 1 to 20 (v/v) % hydrogen. For special applications, the preferred gas mixture can contain from 1 to 10 (v/v) % oxygen and from 3 to 7 (v/v) % hydrogen; or from 1 to 10 (v/v) % hydrogen and from 90 to 99 (v/v) % of argon, helium, nitrogen or mixtures thereof.

The gas mixture is ionized into a plasma having ionization products that include highly destructive components in the form of charged particles and ultra-violet radiation. Preferably, sterilization is effected by employing plasma downstream products consisting essentially of uncharged, highly reactive free radicals, atoms and excited molecules of a gas mixture to sterilize articles. A plasma distribution device blocks the ultra-violet radiation and facilitates the recombination of the charged particles such that essentially uncharged, highly reactive free radicals, atoms and excited molecules of the gas mixture is delivered to the articles or vessels to be sterilized.

The maximum treatment temperature for rapid sterilization is selected to be the highest temperature to which an article can be exposed to the plasma without substantial deterioration. If the article is enclosed in a package including a porous cellulose containing layer, the preselected maximum temperature is preferably up to 63° C., and the plasma gas flow is controlled to maintain the temperature within the range of 63° C. as the preselected maximum temperature. When an unpackaged article includes an organic polymer sensitive to plasma oxidation, the preferred preselected maximum temperature is 82° C. When the article is metal, the preselected maximum temperature can be any temperature which is non-destructive to the metal. A preferred maximum preselected temperature for metal articles is 132° C. In the process of this invention, the temperature below the preselected maximum temperature at which plasma gas flow is reinitiated not more than 3° C. and preferably not more than 2° C. below the preselected maximum temperature.

According to another aspect of the present invention, the article to be sterilized is the interior of a vessel or a chamber and any articles therein. One example of such a chamber would be a lyophilizer which functions as a vacuum chamber for freeze-drying pharmaceutical and medical products. In this application, the lyophilizer chamber is adapted to receive a gas plasma from a plasma generating chamber so that it acts as a sterilization chamber where its interior is to be sterilized. This method is effective and economical since conventional sterilization methods using ethylene oxide or steam have their drawbacks, and the lyophilizer being built as a vacuum chamber, expediently allows adaptation into a plasma sterilizer without the expense of a separate vacuum system.

Additional objects, features and advantages of the present invention will be understood from the following description of the preferred embodiments, which description should be taken in conjunction with the accompanying drawings.

BRIEF DESCRIPTION OF THE DRAWINGS

FIG. 1 is a top view of a plasma sterilizer suitable for use in the process of this invention.

FIG. 2 is a front view of the plasma sterilizer embodiment of FIG. 1.

FIG. 3 is a cross-sectional view of the plasma sterilizer embodiment of FIG. 1 and FIG. 2, taken along the line 3—3 in FIG. 2.

FIG. 4 is a cross-sectional view of the plasma sterilizer embodiment of FIG. 3, taken along the line 4—4.

FIG. 5 is a cross-sectional view of tube 54 taken along line 5—5 in FIG. 3.

FIG. 6 is a cross-sectional view of tube 58 taken along line 6—6 in FIG. 3.

FIG. 7 is a cross-sectional view of tube 56 taken along line 7—7 in FIG. 3.

FIG. 8 is a partial cross-sectional view of the plasma generator tube and assembly of the embodiment of FIG. 1.

FIG. 9 is a partial, fragmentary, cross-sectional detail view of the plasma generator tube of the plasma generator shown in FIG. 8.

FIG. 10 is a cross-sectional view of the waveguide of the embodiment of FIG. 1, taken along the line 10—10 in FIG. 3.

FIG. 11 is a side cross-sectional view of an alternate single waveguide embodiment of the plasma sterilizer suitable for use in the process of this invention.

FIG. 12 is a cross-sectional view of the waveguide of the embodiment of FIG. 11, taken along the line 12—12.

FIG. 13 is a side cross-sectional view of a multiple magnetron embodiment of this invention.

FIG. 14 is a front cross-sectional view of the multiple waveguide embodiment of the plasma sterilizer of this invention, taken along the line 14—14 of FIG. 13.

FIG. 15 is a partial cross-sectional view of the plasma generator tube and assembly of the embodiment of 13.

FIG. 16 is a schematic illustration of adapting a lyophilizer for sterilization.

DETAILED DESCRIPTION OF THE INVENTION

Hospitals originally relied on disinfectants and steam autoclaves for sterilizing implements. In more recent years, ethylene oxide gas sterilization has made possible the sterilization of packaged articles, drugs and medical supplies, and hospital systems are highly dependent upon these procedures. However, ethylene oxide is now known to be a dangerous carcinogen, and a number of new state laws protecting worker safety and the environment are precluding further use of ethylene oxide sterilizers in hospital environments.

Numerous gas plasma sterilizers using a wide variety of gases have been described in the patent literature. A few have been commercially produced. A few have focused on residue contamination problems. The previously described gas sterilizers either fail to satisfy current regulatory residue and exhaust emission safety standards of several states, because they either leave unacceptable residues, produce exhaust emissions which are potentially hazardous to hospital personal, or cause unacceptable destruction of packaging materials.

Substituting one hazard for another, they are thus not satisfactory for replacing ethylene oxide sterilizers.

The process of this invention employs a plasma produced from gas mixtures containing essentially oxidizing agents such as oxygen and/or reducing agents such as hydrogen, and optionally other carrier gases such as inert gases. The exhaust gas products fully satisfy current environmental and worker safety concerns, the products of the plasma being almost entirely water vapor, carbon dioxide and non-toxic gases normally found in the atmosphere.

The term "plasma" as used herein is defined to include any portion of the gas or vapors which contain electrons, ions, free radicals, dissociated and/or excited atoms or molecules produced as a result of the applied electric or electromagnetic field including any accompanying radiation which might be produced. The electromagnetic field can cover a broad frequency range, and can be produced by a magnetron, klystron or RF coil. For purposes of clarity of presentation and not by way of limitation, the description hereinafter describes the use of a magnetron as the electromagnetic field source, and the use of all other suitable sources of the electromagnetic field required for plasma production are intended to be included, including without limitation, magnetrons, klystron tubes, RF coils, and the like. The term "sterilization" connotes a process by which all viable forms of microorganisms are destroyed or removed from an object. Since microorganisms die according to first order chemical kinetics, it is customary to define sterility in terms of "probability of survivors". The practical goal of a sterilization process is therefore measured as a probability (e.g., $10^{-3}$, $10^{-6}$, $10^{-12}$), the probability indicating the lethal effect of a particular sterilizing dose or regimen. It is usual to assume increased time of exposure to a set of sterilizing conditions will decrease the probability of survivors accordingly.

Doubling the sterilizing time of identical conditions would result in a doubling of the exponent of the probability term, for example $10^{-6}$ would become $10^{-12}$. The sterilizing rate with plasma gases is temperature dependent, the rate increasing with increasing temperature. Having a high sterilizing rate increases throughput capacity and reduces time required for return of sterilized goods. However, the corrosive properties of the plasma gases also increase with temperature. An excessive temperature can damage the articles being sterilized. Therefore, maintaining the temperature in the sterilizing chamber at a maximum effective preselected temperature giving the most rapid sterilizing rate consistent with the preservation of the articles being sterilized is an important goal of sterilizing systems.

The method of this invention relies entirely upon the plasma gases for heating the sterilizing chamber. Increased temperature can be achieved by increasing the plasma gas volume entering the chamber or by increasing the plasma gas energy by increasing the electromagnetic energy in the plasma chamber. The antimicrobial kill rate increases with increasing plasma gas energy. In the method of this invention, the plasma gas energy is selected to be more than sufficient to maintain the sterilizing chamber at a desired temperature. The flow of plasma gases is continued until the sterilizing chamber temperature reaches the preselected maximum temperature. The plasma gas flow is then terminated, allowing the temperature in the sterilizing chamber to fall. The temperature drop is preferably of less then 3° C. and optimally less than 2° C. When the lower preselected temperature is reached, the plasma gas delivery to the sterilizing chamber is reinitiated. The temperature rises to the maximum preselected temperature and the plasma gas delivery is discontinued. This plasma cycle is continued until the desired degree of sterilization is obtained. This plasma cycle maintains the sterilizing chamber temperature in a narrow band approximating the most effective sterilizing temperature.

The number of plasma cycles in a full sterilizing cycle depends upon the sterilizing temperature desired, more frequent cycles occurring with the increased heat loss at the higher temperatures and less frequent cycles occurring with the lower heat loss at lower maximum preselected temperatures. The number of plasma cycles is usually more than five.

For sterilizing packaged articles, a preferred cycle comprises exposing an article in a sterilizing chamber to a gas plasma generated in a plasma generating chamber from a mixture of gases consisting essentially of argon, helium, nitrogen or mixtures thereof; from 1 to 21 (v/v) % oxygen; and from 1 to 20 (v/v) % hydrogen. The exposure to the plasma gases is preferably carried out at a pressure of from 0.1 to 10 torr and preferably from 1 to 10 torr. A preferred maximum preselected temperature in the sterilizing chamber is about 63° C. Higher temperatures can be used, provided the time required for effective sterilizing does not cause significant damage to the packaging materials. Then the flow of plasma gases to the sterilizing chamber is terminated until the temperature in the sterilizing chamber falls to not less than 60° C. and preferably not less than 61° C.

For articles including organic polymers which are sensitive to plasma gases, a preselected maximum temperature is about 82° C.

For metal articles or article including organic polymers which are not particularly sensitive to plasma gases, a preselected maximum temperature is about 100° C.

For metal articles such as stainless steel articles, the maximum preselected temperature can be a much higher temperature. A maximum preselected temperature for metal articles is conveniently about 132° C.

At higher temperatures, sterilization is achieved faster (in a flash). Flash sterilizing times obtained with the process of this invention depends upon the temperature and the type of materials comprising the contamination. Flash sterilization is usually achieved with metal articles at temperatures above 100° C. within from 5 to 15 minutes and at higher temperatures up to 135° C. usually within from 2 to 10 minutes.

Plasma gas flow termination is most conveniently effected by deenergizing the magnetron, RF circuit or other plasma generator. If the vacuum pump continues to evacuate the sterilizing chamber while the plasma gas flow is terminated, an unexpected benefit is achieved. The pressure in the sterilizing chamber falls to less than 1 torr and preferably less than 0.1 torr. The pressure rises when the plasma gas flow is reinitiated. This concurrent pressure cycle apparently increases the diffusion of plasma gases through the porous packaging materials, increasing contact of plasma gases with microorganisms and increasing the sterilizing rate.

The process of this invention uses a sterilizing plasma generated from a mixture of oxygen; argon, helium, and/or nitrogen; and hydrogen, or with a mixture of air and hydrogen, supplemented by oxygen or nitrogen to give the desired ratios. The plasma delivery phase of the cycle is carried out at a vacuum pressure of from 0.1 to 10 torr and preferably from 1 to 3 torr.

The method of this invention for plasma sterilization comprises exposing an article to be sterilized to a plasma generated from a gaseous mixture of argon, helium or nitrogen mixed with oxygen and/or hydrogen at the preselected maximum temperature, a pressure of from 0.1 to 10 torr, and a treatment time of at least 5, and preferably from 10 to 15 minutes. For sterilizing packaged goods, the gas mixtures from which the plasma is generated can contain from 1 to 21 (v/v) % oxygen and from 1 to 20 (v/v) % hydrogen, the balance being argon, helium and/or nitrogen and optional small quantities of inert gases.

The gas mixtures producing plasmas for sterilizing packages preferably contain from 1 to 10 (v/v) oxygen and from 2 to 8 (v/v) % hydrogen, and optimally contain from 2 to 8 (v/v) % oxygen and from 3 to 7 (v/v) % hydrogen.

In an alternate embodiment, packaged goods are sterilized by plasma cycled treatment for at least 15 minutes and preferably from 1 to 5 hours with plasma generated from a gas mixture containing from 1 to 10 (v/v) % hydrogen and from 90 to 99 (v/v) % argon, helium and/or nitrogen, with little or no amounts of oxygen being present, the optimum mixture comprising 5 (v/v) % hydrogen and about 95 (v/v) % argon.

In an optimum method of sterilizing, the articles to be sterilized are placed in the sterilizing chamber, supported by conventional grids which permit the plasma to reach all surfaces of the articles. The chamber is closed, the sterilizing chamber is evacuated, plasma generation is begun, and the plasma is directed into and through the sterilizing chamber.

The plasma components have a short life, and quickly decay to form water vapor (gas), carbon dioxide, and other non-toxic components usually found in air. These are fully acceptable as residues or as exhaust gas components.

The pulsed plasma method of this invention can be most effectively used in combination with treatment cycles comprising exposing the articles to sterilizing antimicrobial vapors or gases described in applications Ser. No. 07/522,271 filed May 11, 1990, now abandoned and Ser. No. 07/522,421 filed May 11, 1990, now abandoned; and U.S. Pat. No. 5,084,239 by Bryant A. Campbell, Kern A. Moulton, and Ross A. Caputo entitled PLASMA STERILIZING PROCESS WITH PULSED ANTIMICROBIAL AGENT TREATMENT.

The method of this invention can be carried out in any type of plasma sterilizer, including sterilizers wherein the sterilization is carried out by exposure of an article to the electromagnetic field of the plasma generator. The preferred plasma sterilizers for use in the process of this invention have a plasma generating chamber separate from the sterilizing chamber, and the gas plasma products flow from the plasma generating chamber into the sterilizing chamber containing an article to be sterilized.

One suitable apparatus is shown in FIG. 1. FIG. 1 is a top view and FIG. 2 is a front view of a single waveguide plasma sterilizer embodiment of this invention. The plasma sterilizer has a plasma generator 2 and a sterilizing chamber 4. The plasma generator 2 comprises an electromagnetic field generator such as a magnetron 6 and a waveguide 8 which directs the electromagnetic field. The plasma source gases are directed into plasma generating and delivering tubes 10, 12, and 14 by feeder tubes from gas delivery tubes 16, 18 and 20 leading from the control valve complex 22. Individual gases are fed from the pressured gas sources (not shown) by inlet lines 24, 25 and 26. The operation of the control valves in valve complex 22 is controlled by the central processing unit (CPU) 28 by standard procedures. The control valves and CPU can be any of the conventional, standard devices used for gas flow control in plasma generating equipment.

The sterilizing chamber 4 comprises top plate 30, side plates 32 and 34, bottom plate 36, back plate 37 and front sealing door 38 through which articles or materials to be sterilized are placed in the chamber. The plates are attached together in a sealed relationship to form a vacuum chamber, such as by welding. The door 38 is secured in a sealed relationship with the sterilizing chamber. It is hinged at the top, side or bottom with conventional hinge pins (structure not shown) to swing against abutting surfaces and an O-ring seal 40 (FIG. 3) of the side, top and bottom plates, where the pressure difference between the internal chamber vacuum pressure and the surrounding atmospheric pressure holds it tightly in place.

The plates and door can be made of any material having the strength required to withstand the external atmospheric pressure when the chamber is evacuated. Stainless steel or aluminum plates and door are preferred. The internal surface material of the chamber is critical and greatly affects the number of killing species available in the chamber. A suitable material is pure (98%) aluminum which can be applied either as a liner or as a flame-sprayed coating on all internal walls of the stainless steel chamber. An alternate material is nickel. An optimum material is an inert polymer such as polytetra-fluoroethylene (TEFLON).

Optionally, antimicrobial additives are added as a liquid or vapor through conduit 35 to inlet port 39 (FIG. 4).

The gases are exhausted from the sterilizing chamber through exhaust outlet port 42 to a conventional vacuum pump system (not shown).

FIG. 3 is a top cross-sectional view of the plasma sterilizer embodiment of FIG. 1 and FIG. 2, taken along the line 3—3 in FIG. 2. FIG. 4 is a side cross-sectional view of the plasma sterilizer embodiment of FIG. 1 and FIG. 3, taken along the line 4—4 in FIG. 3. Each of the plasma generators 10, 12 and 14 comprise an inlet cap 44 with gas inlet ports 46, 48 and 50 leading to a respective gas generator tube 51, 52 or 53 leading through the waveguide 8. In the waveguide 8, the gases are energized and convert in tubes 51, 52 and 53 to a plasma. The gas generator tube directs the plasma flow into the gas distribution tubes 54, 56 and 58 from which the plasma is fed into the sterilizing chamber 60. The gas generator tubes are enclosed in tubular metal cooling tubes 62 and 64. The caps 44 and the cooling tubes 62 and 64 are preferably provided with grooves or cooling fins (not shown) in a conventional manner to increase their efficiency in removing heat from gas generator tubes.

The distal end of tubes 51, 52 and 53 have increased thickness and forms a smooth surfaced venturi restriction 96 of reduced cross-sectional area. Cap 98 positioned on the proximal end of plasma distribution tube 56 has a preselected restrictive opening 99 of further reduced cross-sectional area. These restrictions are critical aspects of the preferred embodiment of this invention, allowing different gas pressures in the plasma generating chamber and the sterilization chamber, thereby allowing the operating pressures in the two chambers to be independently optimized.

The diameter of the restrictive opening 99 is selected to maintain a back pressure of from 0.1 to 150 torr and preferably from 1 to 40 torr in the plasma generating zone, with a vacuum chamber pressure in the range of from 0.01 to 100 torr and preferably from 0.1 to 15 torr. This pressure provides optimum energy transfer from the electromagnetic field to the gases with gas mixtures containing oxygen; argon, helium and/or nitrogen; and/or hydrogen and is a major factor for the production of a high yield of plasma at a minimum temperature and with the minimum power requirement achieved with the device of this invention.

The distal ends of the gas distribution tubes 54, 56 and 58 are supported by spring-biased end supports 66 mounted on sideplate 32.

The door 38 is held in sealing engagement by atmospheric pressure against the O-ring seal 40 mounted in the flange 41 extending from the side plates 32 and 34, and the top and bottom plates 30 and 36 (not shown). Optionally, additional conventional closure clamps or latches can be used to insure closure of the door before chamber evacuation is initiated.

FIG. 5, FIG. 6 and FIG. 7 are cross-sectional views of gas distribution tubes 54, 58 and 56, respectively, showing angular positions of the gas distribution outlet ports. The outlet ports are positioned to provide plasma flow to all lower portions of the sterilizing chamber 60 where articles to be sterilized are placed. Tube 54 shown in FIG. 5 is placed adjacent back plate 37 and directs plasma gases downward and toward the lower center of the chamber through outlet ports 70 and 72, respectively. Tube 58 shown in FIG. 6 is placed adjacent the door 38 and directs plasma gases downward and toward the lower center of the chamber through outlet ports 74 and 76, respectively. Tube 56 shown in FIG. 7 is placed in the central portion of the chamber 60 and directs plasma gases laterally downward through outlet ports 78 and 80. The outlet ports shown for the distribution tubes are representative and can be changed to any other configuration which achieves optimal plasma distribution to the sterilizing zone or zones of the chamber. Although only one angular arrangement is shown, each tube can have more than one angular set of outlet ports, each having different angles, along the length of the tube, as desired. The choice of outlet port angles and locations should be selected in view of how the articles to be sterilized are to be placed in the chamber and the type of article to be sterilized.

The plasma is directed through a change of direction, preferably at least 90°, before discharging it into the sterilizing chamber. This prevents direct impingement of hot plasma onto the articles being sterilized, greatly reducing the oxidation of sensitive packaging materials by the activated oxygen atoms in the plasma. Allowing the plasma gases to impinge instead on any relatively cool part of the distribution tubes or sterilizing chamber will have the effect of cooling the gases, which will in turn keep the articles and packaging cool, which will reduce oxidation.

FIG. 8 is a partial top cross-sectional detail fragmentary view of plasma generator tube 12 of FIG. 3, and FIG. 9 is a more detailed view of the plasma generator tube outlet assembly shown in FIG. 3. The gas inlet ports 46 and 50 in the gas inlet cap 44 are connected by passageways 82 and 84 to the gas inlet passageway 86 leading from inlet port 48. The gases fed to the inlet ports are mixed in the passageway 86. The gas mixture passes into the proximal end of the tube 52 and through the excitation zone 87 within the waveguide 8 where the plasma is formed. The proximal end of the plasma generator tube 52 is supported on cylindrical projection 88. O-ring 90 or another type of seal forms a gas-tight seal therewith, thereby maintaining a reduced pressure in the tube 52 and preventing leakage of atmospheric gas into the system.

In this sectional view, an optional plasma starter ionizer is shown. The tip 81 is connected by an insulated conduit 83 (shown schematically) to a power supply 85 which can be powered with a standard 115 V AC power source. A ground conduit 89 from the power supply connects to the gas inlet cap 44. The electric field ionizes a portion of the gas molecules flowing from opening 48 through passageway 86, the ionized gases quickly supporting a plasma as the gases pass through the zone 87. The ionizer can be placed in any of the inlet gas passageways of any of the embodiments of this invention.

Referring to FIG. 9, the outer surface 92 of the distal end of the plasma generator tube 52 is tapered inward and is sealed by O-ring 94 or other form of seal with the backplate 37. The distal end of tube 52 has increased thickness and forms a smooth surfaced venturi restriction 96 of reduced cross-sectional area. Cap 98 positioned on the proximal end of plasma distribution tube 56 has a preselected restrictive opening 99 of further reduced cross-sectional area. These restrictions are critical aspects of the preferred embodiment of this invention, creating a pressure difference between the low pressure plasma generating zone 87 and the vacuum pressure in the distribution tube 56 and sterilizing chamber 60.

The diameter of the restrictive opening 99 is selected to maintain a back pressure of from 0.1 to 150 torr, preferably from 1 to 40 torr in the plasma generating zone with a vacuum chamber pressure in the range of from 0.01 to 100 torr, preferably from 0.1 to 15 torr. This pressure provides optimum energy consumption and plasma generation with gas mixtures containing oxygen; argon, helium and/or nitrogen; and/or hydrogen and is a major factor for the production of a high yield of plasma at a minimum temperature and with the minimum power requirement achieved with the device of this invention.

FIG. 10 is a cross-sectional view of the waveguide of the embodiment of FIG. 1, taken along the line 10—10 in FIG. 3. The waveguide is formed of top and bottom plates 100 and 102, side plates 104 and 106 (FIG. 3), and end plates 108 and 110, welded or bolted together. A single magnetron rod 112 is placed in the end of the waveguide 8. The plasma generating tubes 51, 52 and 53 are positioned in the waveguide 8. The positions of the plasma generating tubes are selected to provide maximum conversion of the electromagnetic field energy to plasma. Tube 53 is positioned in a zone to interact with a third of the field and not with zones of the field which will interact with tubes 51 and 52. Tube 52 is positioned in a zone to interact with a third of the field (half of the remaining field) and not with the field zone which will interact with tube 51. Tube 51 is positioned to interact maximally with the remainder of the field. With this configuration, a single magnetron can be used to generate plasma with a plurality of gas generating tubes. The precise placement of the tubes which will accomplish this result will depend upon the dimensions of the wave guide and the wavelength or frequency of the energizing wave.

Three tubes have been shown in FIG. 10 by way of example and not by way of limitation. Any number, odd or even, of tubes can be used up until the total power of the electromagnetic field is absorbed.

FIG. 11 is a front cross-sectional view of an alternate single wave guide embodiment of the plasma sterilizer of this invention. Three plasma generating units 120 are positioned above the sterilizing chamber 122 defined by upper plate 124, lower plate 126, back plate 128, back plate 130 and side plates 128 and 132. The door plate (not shown) can be mounted to the front of the chamber as described above with respect to FIG. 2 and FIG. 3 and forms a sealed engagement with the front edges of the chamber walls. The gases are exhausted from the chamber through exhaust ports 136 in the floor plate 126.

The plasma generators comprise an inlet port for mixed gases 138 leading to the plasma generating tubes 139, 140 and 141 positioned in the waveguide 142 where the gases are energized and converted to a plasma. The plasma is directed by the plasma distributors 144 to the interior of the sterilizing chamber 122. Each plasma distributor 144 can have a T-configuration described below in detail with respect to the embodiment of FIG. 14. The distributor can have any shape and size which distributes the plasma gases uniformly throughout the sterilizing chamber. The plasma generating source in this embodiment is a magnetron 146 positioned at the end of the waveguide 142.

FIG. 12 is a cross-sectional view of the waveguide of embodiment of FIG. 11, taken along line 12—12 in FIG. 11. The waveguide is formed of top and bottom plates 150 and 152 (FIG. 11), side plates 154 and 156, and end plates 158 and 160, welded or bolted together. A single magnetron rod 162 is placed in the end of the waveguide 142. The plasma generating tubes 139, 140 and 141 are positioned in the waveguide 142. The positions of the plasma generating tubes are selected to provide maximum conversion of the electromagnetic field energy to plasma. Tube 141 is positioned in a zone to interact with a third of the field and not with zones of the field which will interact with tubes 140 and 139. Tube 140 is positioned in a zone to interact with a third of the field (half of the remaining field) and not with the field zone which will interact with tube 139. Tube 139 is positioned to interact maximally with the remainder of the field. With this configuration, a single magnetron can be used to generate plasma with a plurality of gas generating tubes. The precise placement of the tubes which will accomplish this result will depend upon the dimensions of the wave guide and the wavelength or frequency of the energizing wave. Three tubes have been shown in FIG. 12 by way of example and not by way of limitation. Any number, odd or even, of tubes can be used up until the total power of the electromagnetic field is absorbed.

The detailed construction of the plasma generator tube and plasma distribution tube seals and flow restrictors have the same configuration as the corresponding elements in the embodiment of FIG. 11 and are described in greater detail hereinabove in conjunction therewith.

FIG. 13 is a front cross-sectional view of a multiple magnetron embodiment s invention, and FIG. 14 is a side cross-sectional view taken along the line 14—14 in FIG. 13. Three plasma generators 208 of this embodiment are positioned above the sterilizing chamber cavity 229, each producing a plasma generated from a gas mixture of oxygen; argon, helium and/or nitrogen; and/or hydrogen introduced through inlets 210 to a plasma generating tube 230 positioned in the respective waveguides 202. The plasma produced is fed by plasma generating tubes 230 through respective gas distributors 211, 212 and 213 into the sterilizing chamber 229. The distributor tubes can have any length and configuration required for distributing the plasma gases uniformly throughout the sterilizing chamber. Distribution tubes made of non-fragile materials are particularly advantageous. Suitable non-fragile tubes can be made of oxidation resistant metals such as stainless steel. An optimum material is an inert polymer such as polytetra-fluoro-ethylene (TEFLON).

The sterilizing chamber 229 is constructed from metal plates welded to form a gas-tight construction which is able to withstand external pressures when the chamber is evacuated. The construction comprises top plate 214, bottom plate 216, back plate 218, side plates 217 and 219. Exhaust ports 222 are mounted in the bottom plate 216. The door 224 is supported by conventional pin hinges or the like (not shown) mounted on the side, top or bottom of the chamber walls as described above with respect to the embodiment of FIG. 1. The door 224 is held in sealing engagement by atmospheric pressure against the O-ring seal 225 mounted in the flange 227 extending from the side plates 217 and 219, and the top and bottom plates 214 and 216 (not shown). Optionally, additional conventional closure clamp or latch devices can be used to insure closure of the door before chamber evacuation is initiated.

Referring to FIG. 14, the oxygen; argon, helium and/or nitrogen; and/or hydrogen gases are fed by inlet lines 228, 231 and 232 to the control valve and gas mixing unit 233 controlled by CPU 234. The gas mixture is fed to the inlet port 210 by conduit 235 and then to the plasma generating tube 230 where it is energized to form a gas plasma. The control valves and CPU can be any of the conventional, standard devices used for gas flow control in plasma generating equipment. The waveguide 202 guides the electromagnetic waves generated by the magnetron 206 in a pattern which concentrates the electromagnetic energy in a zone in which the plasma generator tube 230 is positioned. A tuning rod 240 can be vertically positioned to tune the electromagnetic waves to provide optimum plasma generation. The gas plasma is then fed to the gas distributor 212 and its Y-or T-distribution section 241. The horizontal distributors have angular outlet ports positioned and with angular displacement as described with respect to the preferred embodiment of FIG. 5, FIG. 6 and FIG. 7. The plasma is directed through a change of direction of 90° twice before it is discharged into the sterilizing chamber. This prevents direct impingement of hot nascent plasma onto the articles being sterilized, greatly reducing the oxidation of sensitive packaging materials by the activated oxygen atoms in the plasma.

FIG. 15 is a fragmentary, cross-sectional view of the plasma generating tube of the plasma generator shown in FIG. 14, showing details of the tube construction and its connection with the gas distributor tube. The tube 230 is held in a sealed engagement with the heat radiating cap 250 by O-ring 252 or a similar seal. The lower distal end of the tube is also held in a sealed engagement with the lower heat radiator sleeve 254 by an O-ring 256. The proximal end of the distribution tube 212 extends into the distal end of tube 230 and is held in a sealed relationship with the lower heat radiator sleeve by an O-ring 258. Cap 260 is positioned on the proximal end of plasma distribution tube 212 and has a preselected restrictive opening 262 of further reduced cross-sectional area. As described with respect to the embodiment shown in FIG. 9, the restriction is a critical aspect of the invention, creating a pressure difference between the low pressure plasma generating zone and the vacuum pressure in the distribution tube and sterilizing chamber.

The diameter of the restrictive opening 262 is selected to maintain a back pressure of from 0.1 to 150 torr, preferably from 1 to 40 torr in the plasma generating zone with a vacuum chamber pressure in the range of from 0.01 to 100 torr, preferably from 0.1 to 15 torr. This pressure provides optimum energy consumption and plasma generation with gas mixtures containing oxygen; argon, helium and/or nitrogen; and/or hydrogen and is a major factor for the production of a high yield of plasma at a minimum temperature and with the minimum power requirement achieved with the device of this invention.

The plasma sterilizer embodiments suitable for use in the process of this invention have been presented with three plasma generating units. The number of generating units is not critical, being selected to provide a good plasma distribution in the particular sterilizing chamber used. Any desired number of plasma generators can be used with each sterilizing chamber and are intended to be included within the scope of this invention. It will be also readily apparent that any number of gas plasma tubes can be positioned to interact with the electromagnetic field generated from a single magnetron with this waveguide configuration, and that other waveguide configurations can be used to achieve this effect. The preferred plasma generating tubes and plasma distributing tubes are made of quartz. However, any other materials with the necessary physical, chemical and electrical properties for plasma generation in an electromagnetic field can be used for the plasma generating tubes. Similarly, the conduits and tubing used for transport of plasma from the plasma generator to the sterilizing chamber can be any solid material which has the requisite shape and strength and which is resistant to chemical action and degradation by the plasma gases. Suitable transport conduit materials include quartz and other plasma corrosion resistant glasses; stainless steel and other oxidation resistant metals; oxidation resistant plastics such as fluorocarbon polymers, e.g. TEFLON and the like, and siloxane polymers.

The plasma is directed through a change of direction, preferably at least 90°, before discharging it into the sterilizing chamber. This prevents direct impingement of hot plasma onto the articles being sterilized. The gas distributors also allow ions to recombine by collisions with their surfaces and allow the UV radiation to dissipate.

The apparatus can be used to generate a sterilizing plasma from a mixture of oxygen; argon, helium, and/or nitrogen; and hydrogen, or with a mixture of air and hydrogen, supplemented by oxygen or nitrogen to give the desired ratios. The sterilization is carried out at a vacuum pressure of from 0.01 to 15 torr and preferably from 0.1 to 15 torr. Sterilization may be carried out at higher pressures provided steps are taken to ensure uniformity of gas flows and temperature throughout the chamber. The temperature in the sterilizing chamber is maintained below 80° C. and preferably from 38° to 60° C. for articles that can not tolerate high temperatures. Elevated temperatures may preferably be used with articles capable of withstanding them.

The apparatus disclosed herein is capable of producing plasma having uncharged, highly reactive species. For example, in the plasma generating chamber, oxygen is energized by microwave radiation and forms a plasma having an initial high concentration of ions and ultraviolet emissions. These are not allowed into the sterilization chamber as they tend to be strongly destructive on the article to be sterilized, or the packaging. The UV emissions are localized in the plasma generating chamber and are attenuated by the restriction means and the plasma distribution means before they reach the sterilizing chamber. Similarly, as high energy ions hit the restriction means and the internal wall of the plasma distribution means, they recombine with free electrons to revert to uncharged, highly reactive free radicals. By the time the plasma enters the sterilizing chamber, the plasma's downstream products include high concentration of highly reactive uncharged free radicals, uncharged atoms and excited molecules.

Typically, a microwave source is used to generate the plasma. It is channeled by a waveguide to form a highly confined electromagnetic (EM) field zone. Little of that field can spread to the sterilizing chamber. Thus, production of high energy ions and UV is only possible in the field region of the plasma generating chamber and not outside of it. Also, there is no EM field to cause non-uniformity in the sterilizing chamber. The restriction means, apart from obstructing the passage of UV and ions as noted above, further helps to make plasma generation outside the plasma generating chamber less favorable. The restriction means maintains an optimal gas pressure in the plasma generating chamber for generating plasma. Once the gas exits via the restriction means, the pressure and the EM field drop to make generation impossible under normal conditions. Thus, UV and ions can only be generated in the plasma generating chamber; once outside, they are allowed to dissipate to form a downstream plasma consisting essentially of energized, highly reactive uncharged free radicals, atoms and excited molecules.

Under these conditions, effective sterilization is effected without significant deterioration of packaging materials in which articles to be sterilized may be placed.

The method of this invention for plasma sterilization comprises exposing an article to be sterilized to a plasma generated from a gaseous mixture of argon, helium or nitrogen mixed with oxygen and/or hydrogen at temperatures of less than 60° C., a pressure of from 0.01 to 100 torr, preferably from 0.1 to 15 torr and a treatment time of at least 5, and preferably from 10 to 15 minutes. For sterilizing packaged goods, the gas mixtures from which the plasma is generated can contain from 1 to 21 (v/v) % oxygen and from 1 to 20 (v/v) % hydrogen, the balance being argon, helium and/or nitrogen and optional small quantities of inert gases.

The gas mixtures producing plasmas for sterilizing packages preferably contain from 1 to 10 (v/v) % oxygen and from 2 to 8 (v/v) % hydrogen, and optimally contain from 2 to 8 (v/v) % oxygen and from 3 to 7

(v/v) % hydrogen. Packages are treated for at least 15 minutes and preferably from 1 to 5 hours.

In an alternate embodiment, packaged goods are sterilized by treatment for at least 15 minutes and preferably from 1 to 5 hours with plasma generated from a gas mixture containing from 1 to 10 (v/v) % hydrogen and from 90 to 99 (v/v) % argon, helium and/or nitrogen, with little or no amounts of oxygen being present, the optimum mixture comprising 5 (v/v) % hydrogen and about 95 (v/v) % argon.

Objects which are resistant to oxidation such as metallic surgical instruments can be sterilized by treatment for at least 1 minute and preferably for at least 5 minutes with plasma generated from a gas mixture containing from 10 to 40 (v/v) % oxygen; from 60 to 90 (v/v) % argon, helium and/or nitrogen; and optional amounts of hydrogen and/or inert gases at a pressure of from 0.01 to 100 torr, preferably from 0.1 to 15 torr. The plasma can be generated from air (21 v/v % oxygen, 78 v/v % nitrogen, etc.), for example.

It is to be understood that the operating temperature of the present process is determined by the characteristics of the articles being sterilized, not by temperature limitations of the sterilization process. Many medical articles to be sterilized will not withstand temperature over 60° C., while other articles such as metallic surgical instruments are more efficiently sterilized at higher temperatures.

Similarly, the pressure limitations given are examples illustrative of the preferred embodiments. Different pressure limits are contemplated for other plasma sterilizers having different dimensions and surface characteristics.

A processing time of from 5 to 10 minutes is usually sufficient to sterilize most articles. Clean articles packaged in envelopes or other shapes having porous surfaces allowing easy penetration of the plasma are usually completely sterilized within 60 minutes.

In an optimum method of sterilizing, the articles to be sterilized are placed in the sterilizing chamber, supported by conventional fixtures which permit the plasma gas products to reach all surfaces of the articles. The chamber is closed, the sterilizing chamber is evacuated, plasma generation is begun, and the plasma gas products are directed into and through the sterilizing chamber.

The plasma components have a short life, and quickly decay to form water vapor (gas), carbon dioxide, and other non-toxic components usually found in air. These are fully acceptable as residues or as exhaust gas components.

One application of the present invention is to sterilize lyophilizers. Lyophilizers are essentially large vacuum chambers (e.g., 5 to 30 cubic ft.) used to freeze dry solutions or liquid suspensions. In the medical industry they are used primarily to freeze dry pharmaceuticals for preservation.

FIG. 16 is a schematic illustration of a lyophilizer adapted to be sterilized by the plasma process of the present invention. The lyophilizer system 300 includes a lyophilizer chamber 312, a condenser 314 and a vacuum pump 316. The vacuum pump 316 is capable of evacuating the lyophilizer chamber 312 via a vacuum line 322, the condenser 314 and another vacuum line 324. Typically, the material or articles to be dried (which may be frozen) are held in containers and loaded into the lyophilizer chamber 312. After the door or the lyophilizer chamber (not shown) is sealed, the interior of the lyophilizer is evacuated using the vacuum pump 316. The material or articles cool (and freeze, if they are not already frozen) as water evaporates. The evaporated water is mostly condensed by the condenser 314 and removed. Further pumping causes water in the material or articles to sublime until substantially all the water is removed. When the process is complete, the lyophilizer chamber 312 is vented and the containers are removed.

Lyophilizers used to prepare pharmaceuticals must be sterilized after each batch. Conventional methods of using heat or ethylene oxide are problematic. As mentioned earlier, ethylene oxide is a carcinogen and great precautions must be exercised in its use. Adapting the lyophilizer to steam sterilization raises considerations such as condensation problem and ability of the lyophilizer to withstand high temperature (e.g., 121° C.) and high internal pressure (e.g., 15 psig).

According to one aspect of the present invention, a plasma generating system 330 includes a plasma generating chamber 332. The lyophilizer chamber is connected to receive a gas plasma from the plasma generating chamber 332 via a port 340 and connecting tube 342. During the plasma sterilization process, the lyophilizer chamber acts as a sterilizing chamber with the evacuation provided by the vacuum pump 316.

In one embodiment, the interior of the lyophilizer chamber is sterilized by the gas plasma. In another embodiment, both the interior of the lyophilizer chamber and the material or articles therein after completion of lyophilization are subjected to the gas plasma for sterilization.

For a large capacity lyophilizer, distributing gas plasma via a single port or location to the interior of the lyophilizer chamber 312 may led to nonuniformity. One or more internally fitted gas distributors such as that shown in FIGS. 3, 4, 11–14 are preferable. In other embodiments, additional ports such as 340', 340" and 340"' and additional connecting tubes such as 342', 342" and 342"' connected to the plasma generating chamber 332 are used to introduce the gas plasma into various regions of the lyophilizer chamber 312.

As described earlier and also in U.S. Pat. No. 5,084,239, a treatment by an antimicrobial agent is optionally used in combination with the plasma process to effect sterilization. This is accomplished by feeding antimicrobial agent such as peracid vapor from an antimicrobial agent source 350 from a line 352 into the lyophilizer chamber 312 via one or more of the ports and connecting tubes.

While the embodiments of the various aspects of the present invention that have been described are the preferred implementation, those skilled in the art will understand that variations thereof may also be possible. Therefore, the invention is entitled to protection with in the scope of the appended claims.

We claim:

1. A method for plasma sterilization of an interior of a chamber and any articles therein within a controlled temperature range comprising:
   a) exposing the interior of said chamber and any articles therein to a gas plasma flowing from a plasma generating chamber until the temperature in said chamber rises to a preselected maximum temperature;
   b) terminating flow of the gas plasma to said chamber until the temperature in said chamber falls to a preselected temperature below the preselected maximum temperature; and c) repeating steps (a) and (b) until sterilization of the interior of said chamber and any articles therein as defined by a preselected probability of survivors is effected; and wherein said any articles in said chamber are enclosed in porous packaging.

2. A method for plasma sterilization of an interior of a chamber and any articles therein within a controlled temperature range comprising:
 a) exposing the interior of said chamber and any articles therein to a gas plasma flowing from a plasma generating chamber until the temperature in said chamber rises to a preselected maximum temperature;
 b) terminating flow of the gas plasma to said chamber until the temperature in said chamber falls to a preselected temperature below the preselected maximum temperature; and
 c) repeating steps (a) and (b) until sterilization of the interior of said chamber and any articles therein as defined by a preselected probability of survivors is effected; and wherein the preselected maximum temperature does not exceed 132° C.

3. A method for plasma sterilization of an interior of a chamber and any articles therein within a controlled temperature range comprising:
 a) exposing the interior of said chamber and any articles therein to a gas plasma flowing from a plasma generating chamber until the temperature in said chamber rises to a preselected maximum temperature;
 b) terminating flow of the gas plasma to said chamber until the temperature in said chamber falls to a preselected temperature below the preselected maximum temperature; and
 c) repeating steps (a) and (b) until sterilization of the interior of said chamber and any articles therein as defined by a preselected probability of survivors is effected; and wherein:
 the step of exposing the interior of said chamber and any articles therein to a gas plasma is performed at a pressure of from 0.01 to 100 torr, until the temperature in said chamber rises to about 63° C.; and
 the step of terminating flow of gas plasma to said chamber is performed as long as the temperature in said chamber remains above 60° C., said chamber having a reduced pressure when the plasma gas flow is terminated.

4. A method for plasma sterilization of an interior of a chamber and any articles therein within a controlled temperature range comprising:
 a) exposing the interior of said chamber and any articles therein to a gas plasma flowing from a plasma generating chamber until the temperature in said chamber rises to a preselected maximum temperature;
 b) terminating flow of the gas plasma to said chamber until the temperature in said chamber falls to a preselected temperature below the preselected maximum temperature; and
 c) repeating steps (a) and (b) until sterilization of the interior of said chamber and any articles therein as defined by a preselected probability of survivors is effected; and wherein the gas plasma is generated from a mixture of gases including an oxidizing agent.

5. A method for plasma sterilization of an interior of a chamber and any articles therein within a controlled temperature range comprising:
 a) exposing the interior of said chamber and any articles therein to a gas plasma flowing from a plasma generating chamber until the temperature in said chamber rises to a preselected maximum temperature;
 b) terminating flow of the gas plasma to said chamber until the temperature in said chamber falls to a preselected temperature below the preselected maximum temperature; and
 c) repeating steps (a) and (b) until sterilization of the interior of said chamber and any articles therein as defined by a preselected probability of survivors is effected; and wherein the gas plasma is generated from a mixture of gases including a reducing agent.

6. A method for plasma sterilization of an interior of a chamber and any articles therein within a controlled temperature range comprising:
 a) exposing the interior of said chamber and any articles therein to a gas plasma flowing from a plasma generating chamber until the temperature in said chamber rises to a preselected maximum temperature;
 b) terminating flow of the gas plasma to said chamber until the temperature in said chamber falls to a preselected temperature below the preselected maximum temperature; and
 c) repeating steps (a) and (b) until sterilization of the interior of said chamber and any articles therein as defined by a preselected probability of survivors is effected; and wherein the gas plasma is generated from a mixture of gases including oxidizing and reducing agents.

7. A method for plasma sterilization of an interior of a chamber and any articles therein within a controlled temperature range comprising:
 a) exposing the interior of said chamber and any articles therein to a gas plasma flowing from a plasma generating chamber until the temperature in said chamber rises to a preselected maximum temperature;
 b) terminating flow of the gas plasma to said chamber until the temperature in said chamber falls to a preselected temperature below the preselected maximum temperature; and
 c) repeating steps (a) and (b) until sterilization of the interior of said chamber and any articles therein as defined by a preselected probability of survivors is effected; and wherein said any articles in said chamber are unpackaged, and the preselected maximum temperature does not exceed 132° C.

8. A method for plasma sterilization of an interior of a chamber and any articles therein within a controlled temperature range comprising:
 a) exposing the interior of said chamber and any articles therein to a gas plasma flowing from a plasma generating chamber until the temperature in said chamber rises to a preselected maximum temperature;
 b) terminating flow of the gas plasma to said chamber until the temperature in said chamber falls to a preselected temperature below the preselected maximum temperature; and c) repeating steps (a) and (b) until sterilization of the interior of said chamber and any articles therein as defined by a preselected probability of survivors is effected; and wherein said chamber is a lyophilizer.

9. A method of claim 8 wherein the gas plasma is generated from a mixture of gases including argon, helium, nitrogen or mixtures thereof; from 1 to 21 (v/v) % oxygen; and from 1 to 20 (v/v) % hydrogen.

10. A method of claim 8 wherein said chamber initially has a pressure of greater or equal to 0.01 torr and rises to not more than 100 torr when the gas plasma is flowing into said chamber.

11. A method of claim 8 wherein said chamber has a pressure that falls when the gas plasma flow into said chamber is terminated.

12. A method of claim 11 wherein said chamber has a pressure that rises to above 1 torr when the gas plasma is flowing into said chamber and falls below 1 torr when the gas flow into said chamber is terminated.

13. A method of claim 8 wherein said any articles in said chamber are enclosed in porous packaging.

14. A method of claim 8 wherein said any articles in said chamber include an organic polymer, and the preselected maximum temperature does not exceed 82° C.

15. A method of claim 8 wherein the preselected maximum temperature does not exceed 132° C.

16. A method of claim 8 wherein the preselected temperature below the preselected maximum temperature is not more than 3° C. below the preselected maximum temperature.

17. A method of claim 8 wherein:
the step of exposing the interior of said chamber and any articles therein to a gas plasma is performed at a pressure of from 0.1 to 100 torr, until the temperature in said chamber rises to about 63° C.; and
the step of terminating flow of gas plasma to said chamber is performed as long as the temperature in said chamber remains above 60° C., said chamber having a reduced pressure when the plasma gas flow is terminated.

18. A method of claim 8 wherein the gas plasma is generated from a gas mixture containing from 1 to 10 (v/v) % oxygen and from 3 to 7 (v/v) % hydrogen.

19. A method of claim 8 wherein said any articles in said chamber are enclosed in porous packaging.

20. A method of claim 8 wherein the gas plasma is generated from a mixture of gases including from 1 to 10 (v/v) % hydrogen and from 90 to 99 (v/v) % of argon, helium, nitrogen or mixtures thereof.

21. A method of claim 8 wherein the gas plasma is generated from a mixture of gases including an oxidizing agent.

22. A method of claim 8 wherein the gas plasma is generated from a mixture of gases including a reducing agent.

23. A method of claim 8 wherein the gas plasma is generated from a mixture of gases including oxidizing and reducing agents.

24. A method of claim 8 wherein said any articles in said chamber are unpackaged, and the preselected maximum temperature does not exceed 132° C.

* * * * *

UNITED STATES PATENT AND TRADEMARK OFFICE
CERTIFICATE OF CORRECTION

PATENT NO. : 5,288,460
DATED : February 22, 1994
INVENTOR(S) : Caputo et al.

It is certified that error appears in the above-indentified patent and that said Letters Patent is hereby corrected as shown below:

On the cover page, [*] Notice:   Replace "Feb. 16, 2010" with --Jan. 10, 2010--

Signed and Sealed this

Thirteenth Day of December, 1994

Attest:

*Bruce Lehman*

BRUCE LEHMAN

*Attesting Officer*     *Commissioner of Patents and Trademarks*